United States Patent [19]
Vora et al.

[11] Patent Number: 5,714,662
[45] Date of Patent: Feb. 3, 1998

[54] PROCESS FOR PRODUCING LIGHT OLEFINS FROM CRUDE METHANOL

[75] Inventors: Bipin V. Vora, Darien; Terry L. Marker, Warrenville, both of Ill.; Henning R. Nilsen, Lier, Norway

[73] Assignee: UOP, Des Plaines, Ill.

[21] Appl. No.: 513,242

[22] Filed: Aug. 10, 1995

[51] Int. Cl.$^6$ ........................................... C07C 1/24
[52] U.S. Cl. ............................................. 585/640; 585/638
[58] Field of Search ................................. 585/640, 638

[56] References Cited

U.S. PATENT DOCUMENTS

| | | | |
|---|---|---|---|
| 3,326,956 | 6/1967 | Davies et al. | 260/449.5 |
| 3,928,483 | 12/1975 | Chang et al. | 260/668 R |
| 4,025,575 | 5/1977 | Chang et al. | 260/682 |
| 4,052,479 | 10/1977 | Chang et al. | 260/682 |
| 4,076,761 | 2/1978 | Chang et al. | 260/668 R |
| 4,440,871 | 4/1984 | Lok et al. | 502/214 |
| 4,447,669 | 5/1984 | Hamon et al. | 585/640 |
| 4,496,786 | 1/1985 | Santilli et al. | 585/640 |
| 4,499,314 | 2/1985 | Seddon et al. | 585/408 |
| 4,547,616 | 10/1985 | Avidan et al. | 585/638 |
| 4,677,242 | 6/1987 | Kaiser | 585/638 |
| 4,677,243 | 6/1987 | Kaiser | 585/638 |
| 4,843,183 | 6/1989 | Inui | 585/640 |
| 4,861,938 | 8/1989 | Lewis et al. | 585/640 |
| 4,973,792 | 11/1990 | Lewis et al. | 585/638 |
| 5,041,690 | 8/1991 | Harandi et al. | 568/695 |
| 5,095,163 | 3/1992 | Barger | 585/640 |
| 5,126,308 | 6/1992 | Barger et al. | 502/214 |
| 5,130,101 | 7/1992 | Harandi et al. | 422/189 |
| 5,191,141 | 3/1993 | Barger et al. | 585/640 |

FOREIGN PATENT DOCUMENTS

WO 93/13013   7/1993   WIPO   .............. C01B 25/45

OTHER PUBLICATIONS

LeBlanc, J.R. Schneider, III, R.V. and Strait, R. B. "Production of Methanol," Cheng, W.H. and Kung, H.H., Eds. of *Methanol Production and Use*, (New York Marcel Dekker, Inc., Publisher 1994) pp. 51–73, 84–93, 111–113.

*Primary Examiner*—Gary Geist
*Assistant Examiner*—Sreeni Padmanabhan
*Attorney, Agent, or Firm*—Thomas K. McBride; John G. Tolomei; Richard P. Silverman

[57] ABSTRACT

A process is disclosed for the production of light olefins from a hydrocarbon gas stream by a combination of reforming, oxygenate production, and oxygenate conversion wherein a crude methanol stream—produced in the production of oxygenates and comprising methanol, light ends, and heavier alcohols—is passed directly to the oxygenate conversion zone for the production of light olefins. Furthermore, the combination provides the synergy for increased catalyst life and reduced water treatment costs by recycling by-product water produced in the oxygenate conversion zone to provide water to the syngas production zone. The advantage of this integration is the elimination of costly methanol separation and purification steps which result in the overall reduction in the costs of producing the light olefins. Other advantages include the reduction in catalyst cost in the oxygenate production zone by the reduction in the catalyst selectivity by the extension of catalyst life in the oxygenate production zone. In addition, a portion of the by-product water can be combined with a propylene stream to provide a high octane blending component for gasoline. The propylene and butylene fractions produced by the above integrated scheme are further converted to high octane ether and other high value products.

30 Claims, 3 Drawing Sheets

PROCESS FOR PRODUCING LIGHT OLEFINS FROM CRUDE METHANOL

FIELD OF THE INVENTION

This invention relates to a process for the production of light olefins from a hydrocarbon feedstream.

BACKGROUND OF THE INVENTION

Light olefins have traditionally been produced through the process of steam or catalytic cracking. Because of the limited availability and high cost of petroleum sources, the cost of producing light olefins from such petroleum sources has been steadily increasing. Light olefins serve as feeds for the production of numerous chemicals. As the emerging economies of the Third World strain toward growth and expansion, the demand for light olefins will increase dramatically.

The search for alternative materials for light olefin production has led to the use of oxygenates such as alcohols, and more particularly to the use of methanol, ethanol, and higher alcohols or their derivatives. These alcohols may be produced by fermentation or from synthesis gas. Synthesis gas can be produced from natural gas, petroleum liquids, and carbonaceous materials including coal, recycled plastics, municipal wastes, or any organic material. Thus, alcohol and alcohol derivatives may provide non-petroleum based routes for the production of olefin and other related hydrocarbons.

Methanol is typically synthesized in the gas phase or liquid phase over a heterogeneous catalyst. The feed to the methanol plant comprises a combination of hydrogen, carbon monoxide and carbon dioxide. The synthesis reactions employed on an industrial scale are as follows:

$$CO + 2H_2 \rightleftharpoons CH_3OH$$

or $$CO_2 + 3H_2 \rightleftharpoons CH_3OH + H_2O$$

The catalyst formulations typically include copper oxide (60–70%), zinc oxide (20–30%) and alumina (5–15%). Chapter 3 of *Methanol Production and Use*, edited by Wu-Hsun Cheng and Harold H. Kung, Marcel Dekker, Inc., New York, 1994, pages 51–73, provides a summary of the current methanol production technology with respect to catalyst, reactors, typical yields operating conditions. The above reference is hereby incorporated by reference.

Methanol is generally produced in what in known as a synthesis loop which incorporates the generation of the synthesis gas. Although synthesis gas may be produced from coal gasification and partial oxidation, the primary route in industry is via the steam reforming of natural gas. The steam reformer is generally a large process furnace in which catalyst-filled robes are heated externally by direct firing to provide the necessary heat for the following reaction, known as the water-gas shift reaction to take place:

$$C_nH_{2n+2} + nH_2O \rightleftharpoons nCO + (2n+1)H_2$$

wherein in the number of carbon atoms per molecule of hydrocarbon. A process known as combined reforming employs both a primary and a secondary reformer in series for the production of synthesis gas. In the secondary reformer, nearly pure oxygen (99.5$^+$%) is injected to combust excess hydrogen to produce a nearly stoichiometric synthesis gas having a stoichiometric ratio of R with a value close to unity where:

$$R = \frac{\text{moles } H_2}{2x \text{ moles CO} + 3 \text{ moles } CO_2}$$

Sections 3.3.3 and 3.3.4 of *Methanol Production and Use*, supra, pages 84–93, describing the production of synthesis gas from natural gas are herein incorporated by reference.

The design of the methanol synthesis loop and associated distillation train to purify the methanol product is generally based on reliability, operability, and capital cost considerations. Crude methanol, as produced by the synthesis section, contains water and impurities which typically must be removed before the methanol product can be used commercially. Crude methanol is generally processed in a multi column system which includes a topping column to remove light ends, such as ethers, ketones, and aldehydes, and dissolved gases such as hydrogen methane, carbon oxide, and nitrogen. The final separation in a refining zone is difficult and requires a large number of distillation stages in one or more columns. Significant energy is required to separate and purify the methanol. Particularly difficult is the ethanol/methanol separation to reach purities of less than 10 ppm ethanol. The higher boiling alcohols are extracted from a point near the bottom of the refining zone while water is removed from the bottom of the column. Sections 3.4.6 of *Methanol Production and Use*, supra, pages 111–113 summarize fractionation options and are hereby incorporated by reference.

Molecular sieves such as the microporous crystalline zeolite and non-zeolitic catalysts, particularly silicoaluminophosphates (SAPO), are known to promote the conversion of oxygenates to hydrocarbon mixtures. Numerous patents describe this process for various types of these catalysts: U.S. Pat. Nos. 3,928,483, 4,025,575, 4,252,479 (Chang et al.); 4,496,786 (Santilli et al.); 4,547,616 (Avidan et al.); 4,677,243 (Kaiser); 4,843,183 (Inui); 4,499,314 (Seddon et al.); 4,447,669 (Harmon et al.); 5,095,163 (Barger); 5,126,308 (Barger); 4,973,792 (Howard); and 4,861,938 (Lewis).

The oxygenate conversion process may be generally conducted in the presence of one or more diluents which may be present in the oxygenate feed in an amount between about 1 and about 99 molar percent, based on the total number of moles of all feed and diluent components fed to the reaction zone (or catalyst). Diluents include—but are not limited to—helium, argon, nitrogen, carbon monoxide, carbon dioxide, hydrogen, water, paraffins, hydrocarbons (such as methane and the like), aromatic compounds, or mixtures thereof. U.S. Pat. Nos. 4,861,938 and 4,677,242 particularly emphasize the use of a diluent combined with the feed to the reaction zone to maintain sufficient catalyst selectivity toward the production of light olefin products, particularly ethylene. The above U.S. Patents are hereby incorporated by reference.

International Patent Application No. 93/13013 to Kvisle et al. relates to an improved method for producing a silico-alumino-phosphate catalyst which is more stable to deactivation by coking. The patent discloses that after a period of time, all such catalysts used to convert methanol to olefin (MTO) lose the active ability to convert methanol to hydrocarbons primarily because the microporous crystal structure is coked; that is, filled up with low volatility carbonaceous compounds which block the pore structure. The carbonaceous compounds can be removed by conventional methods such as combustion in air.

U.S. Pat. No. 4,076,761 to Chang et al. relates to a process for the production of LPG and gasoline from synthesis gas wherein the synthesis gas is derived from fossil fuels. The synthesis gas is passed to a first reaction zone wherein the synthesis gas is catalytically converted to a mixture of methanol and dimethyl/ether which is in turn converted in a separate reaction zone containing a crystalline aluminosilicate zeolite catalyst to a product which is separated into a high octane gasoline fraction, a light hydrocarbon gas fraction, and a hydrogen-rich gas fraction which is recycled to the conversion of fossil fuels to synthesis gas.

U.S. Pat. Nos. 5,130,101 and 5,041,690 to Harandi et al., disclose a process for the conversion of methanol or other alcohol to high octane gasoline components wherein the process comprises passing a crude aqueous alcohol feedstock containing from 2 to 20% water to an extraction zone. In the extraction zone, the feedstock is extracted with a liquid extractant containing $C_4^+$ isoolefin to produce an extract stream containing a sufficient mount of methanol substantially free of water which is then reacted to form tert.-alkyl ethers such as MTBE. The aqueous raffinate lean in methanol is converted to olefinic hydrocarbons in a catalytic reactor zone. Propene from the catalytic reactor zone is reacted with water to produce di-isopropyl ether. Isobutylene and isoamylene from the catalytic reactor zone can be recovered and recycled as the liquid extractant.

Methods are sought to reduce energy and capital cost in the production of light olefins from methanol by taking advantage of the by-products produced in the conversion of carbon oxides to methanol and related oxygenates.

SUMMARY

It has been discovered that significant capital cost and energy savings as well as the additional yield of olefin can be accomplished by the combination of a methanol plant with an oxygenate conversion process. The present invention relates to a process for sending the crude methanol as produced in the methanol plant to the methanol CO olefins process without removing the water or the impurities. The fusel oils in crude methanol, which typically include higher alcohols and are generally burned as a fuel in the methanol plant, are passed to the oxygenate conversion process for the additional production of light olefins in the present invention. In so doing it was found that the yield of ethylene, propylene, and butylenes can be enhanced at significant capital and operating cost savings by not requiring a complex and expensive distillation train for the production of high purity methanol. Furthermore, a problem with carbon oxide conversion units such as methanol plants is that the reactions which produce the oxygenates are highly exothermic and production is often carried out in very large plants at world-scale production rates which are approaching about 7,000 to about 10,000 metric tons per day in a single production train. As a consequence, the carbon oxide conversion catalyst which promotes the reduction reactions is disposed in thin wall tubes, making catalyst replacement expensive and plant downtime for catalyst replacement very costly. By processing crude methanol directly in the oxygenate conversion unit of the present invention, as the carbon oxide conversion catalyst looses its selectivity to methanol in favor of other oxygenates such as dimethyl ether, fusel oils and heavier alcohols as the catalyst ages, the useful life of the carbon oxide catalyst can be extended beyond normal limits for the production of olefins from the oxygenate conversion zone which converts these other oxygenates into light olefins. The synergy provided by the linking of the above operations thereby provides significant water treatment equipment, catalyst, and operating cost savings.

In one embodiment, the invention is a process for the production of light olefins from a hydrocarbon gas feedstream, comprising methane and ethane. The process comprises passing the feedstream in combination with a water stream to a syngas production zone to produce a synthesis gas stream. The synthesis gas stream is passed to an oxygenate formation zone to produce a crude methanol stream comprising methanol, dimethyl ether, and heavier oxygenates. At least a portion of the crude methanol is passed in the presence of a diluent to an olefin production zone containing a small pore catalyst to produce a light olefin stream. The light olefin stream consists essentially of light olefins having from 24 carbon atoms per molecule and water.

DETAILED DESCRIPTION OF THE INVENTION

The hydrocarbon gas feedstream refers to a natural or synthetic natural gas stream such as produced from a natural gas, coal, shale oil, residua or combination thereof. The hydrocarbon gas stream comprises methane and ethane. The hydrocarbon gas stream is passed to a synthesis gas plant wherein impurities such as sulfur compounds, nitrogen compounds, particulate matter, and condensibles are removed in the conventional manner to provide a synthesis gas stream reduced in contaminants and containing a molar ratio of hydrogen to carbon oxide (carbon monoxide plus carbon dioxide). A carbon oxide, as used herein, refers to carbon dioxide and/or carbon monoxide. Synthesis gas refers to a combination of hydrogen and carbon oxides produced in a synthesis gas plant from a hydrocarbon gas derived from natural gas or from the partial oxidation of petroleum or coal residues. Generally, the production of oxygenates, primarily methanol, takes place as a combination of three process steps and a utility section. The three process steps are: synthesis gas preparation, methanol synthesis, and methanol distillation. In the synthesis gas preparation step, the hydrocarbon feedstock is purified to remove sulfur and other potential catalyst poisons prior to being converted into synthesis gas. The conversion to synthesis gas generally takes place at high temperatures over a nickel-containing catalyst to produce a synthesis gas containing a combination of hydrogen, carbon monoxide, and carbon dioxide. Typically, the pressure at which synthesis gas is produced ranges from about 20 to about 75 bar and the temperature at which the synthesis gas exits the reformer ranges from about 700° C. to 1100° C. The synthesis gas contains a molar ratio of hydrogen to carbon oxide ranging from about 2 to about 3, and more typically the molar ratio of hydrogen to carbon oxide varies from about 2.0 to about 2.3. The synthesis gas is subsequently compressed to a methanol synthesis pressure. In the methanol synthesis step, the compressed synthesis gas is converted to methanol, water, and minor mounts of by-products.

The synthesis gas preparation, also known as reforming, may take place in a single-step wherein all of the energy consuming reforming reactions are accomplished in a single tubular steam reformer. The single-step reformer results in a production of surplus hydrogen and a substantial heat surplus. In a preferred alternative, the synthesis gas preparation may take place in a two-step reforming process wherein the primary reforming in a tubular steam reformer is combined with an oxygen-fired secondary reforming step which produces a synthesis gas with a deficiency in hydrogen. With this combination it is possible to adjust the synthesis gas composition to the most suitable composition for methanol synthesis. As an alternative, autothermal reforming—wherein a stand-alone, oxygen-fired reformer produces synthesis gas having a hydrogen deficiency followed by the downstream removal of carbon dioxide to restore the desired ratio of hydrogen to carbon oxide—results in a simplified process scheme with lower capital cost. The burner design is an important part if either oxygen-fired step. The burner mixes the hydrocarbon and oxygen and by combustion in the flame, heat is provided for conversion of the hydrocarbon.

The reaction from synthesis gas to oxygenates such as methanol is an exothermic reaction which is favored by low temperature and high pressure over a heterogeneous catalyst. The reactions which produce methanol exhibit a decrease in volume. As disclosed in U.S. Pat. No. 3,326,956, low-pressure methanol synthesis is based on a copper oxide-zinc oxide-alumina catalyst that typically operates at a nominal pressure of 5–10 MPa and temperatures ranging from about 150° C. to about 450° C. over a variety of catalysts, including $CuO/ZnO/Al_2O_3$, $CuO/ZnO/Cr_2O_3$, $ZnO/Cr_2O_3$, Fe, Co, Ni, Ru, Os, Pt, and Pal. Catalysts based on ZnO for the production of methanol and dimethyl ether are preferred. The low-pressure, copper-based methanol synthesis catalyst is commercially available from suppliers such as BASF, ICI Ltd. of the United Kingdom, and Haldor-Topsoe. Methanol yields from copper-based catalysts are generally over 99.5% of the convened $CO+CO_2$ present as methanol in the crude product stream. Water is a by-product of the conversion of the synthesis gas to oxygenates. A paper entitled, "Selection of Technology for Large Methanol Plants," by Helge Holm-Larsen, presented at the 1994 World Methanol Conference, Nov. 30–Dec. 1, 1994, in Geneva, Switzerland, and herein incorporated by reference, reviews the developments in methanol production and shows how further reduction in costs of methanol production will result in the construction of very large plants with capacities approaching 10,000 metric tonnes per day. Methanol and other oxygenates produced in the above manner are herein further referred to as an oxygenate feedstock.

In accordance with the oxygenate conversion process of the present invention, an oxygenate feedstock is catalytically converted to hydrocarbons containing aliphatic moieties such as—but not limited to—methane, ethane, ethylene, propane, propylene, butylene, and limited amounts of other higher aliphatics by contacting the oxygenate feedstock with a preselected catalyst. The oxygenate feedstock comprises hydrocarbons containing aliphatic moieties such as—but not limited to—alcohols, halides, mercaptans, sulfides, amines, ethers and carbonyl compounds or mixtures thereof. The aliphatic moiety preferably contains from about 1 to about 10 carbon atoms, and more preferably 1 to about 4 carbon atoms. Representative oxygenates include—but are not limited to—methanol, isopropanol, n-propanol, ethanol, fuel alcohols, dimethyl ether, diethyl ether, methyl mercaptan, methyl sulfide, methyl amine, ethyl mercaptan, ethylchloride, formaldehyde, dimethylketone, acetic acid, n-alkylamines, n-alkylhalides, and n-alkyl-sulfides having alkyl groups of 1 to 10 carbon atoms or mixtures thereof. In a preferred embodiment, crude methanol is used as the oxygenate feedstock. As used and described herein, the term "crude methanol" or "crude oxygenate feedstock" designates the effluent from the carbon oxide conversion zone and refers to a stream comprising methanol, ethanol, water, light ends, and fuel offs. The light ends include ethers, ketones, aldehydes, and dissolved gases such as hydrogen, methane, carbon oxide, and nitrogen. The fuel offs include heavier hydrocarbons such as paraffins and higher alcohols. Crude oxygenate feedstock as employed in the present invention and described herein designates only the organic material used as the feed. The total charge of feed to the oxygenate conversion reaction zone may contain additional compounds such as diluents.

A diluent is required to maintain the selectivity of the oxygenate conversion catalyst to produce light olefins, particularly ethylene and propylene. The use of steam as the diluent provides certain equipment cost and thermal efficiency advantages. The phase change between steam and liquid water can be employed to advantage in transferring heat between the feedstock and the reactor effluent, and the separation of the diluent from the product requires simple condensation of the water to separate the water from the hydrocarbons. Ratios of 1 mole of feed to 4 moles of water have been disclosed.

The oxygenate conversion process of the present invention is preferably conducted in the vapor phase such that the crude oxygenate feedstock is contacted in a vapor phase in a reaction zone with a non-zeolite molecular sieve catalyst at effective process conditions to produce hydrocarbons, i.e., an effective temperature pressure, WHSV and, optionally, an effective mount of diluent, correlated to produce olefins having 2 to 4 carbon atoms per molecule. Preferably, the olefins produced by the oxygenate conversion zone consist essentially of ethylene, propylene, and butylene whereby consisting essentially of means that at least 90% of the olefins in the olefin product consist of ethylene, propylene, and butylene. The oxygenate conversion process is affected for a period of time sufficient to produce the desired light olefin products. In general, the residence time employed to produce the desired olefin product can vary from seconds to a number of hours. It will be readily appreciated that the residence time will be determined to a significant extent by the reaction temperature, the molecular sieve selected, the WHSV, the phase (liquid or vapor) and process design characteristics selected. The crude oxygenate feedstock flow rate affects olefin production. Increasing the feedstock flow rate (expressed as weight hourly space velocity, or WHSV) enhances the formation of olefin production relative to paraffin production. However, the enhanced olefin production relative to paraffin production is offset by a diminished conversion of oxygenate to hydrocarbons.

The oxygenate conversion process is effectively carried out over a wide range of pressures, including autogenous pressures. At pressures between about 0.001 atmospheres (0.76 torr) and about 1000 atmospheres (760,000 torr), the formation of light olefin products will be affected although the optimum amount of product will not necessarily form at all pressures. The preferred pressure is between about 0.01 atmospheres (7.6 torr) and about 100 atmospheres (76,000 torr). More preferably, the pressure will range from about 1 to about 10 atmospheres. The pressures referred to herein for the oxygenate conversion process are exclusive of the inert diluent, if any, that is present and refer to the partial pressure of the feedstock as it relates to oxygenate compounds and/or mixtures thereof. Pressures outside the stated range are not excluded from the scope of this invention, although such do not fall within certain desirable embodiments of the invention. At the lower and upper end of the pressure range and beyond, the selectivities, conversions and/or rates to light olefin products may not occur at the optimum, although light olefin such as ethylene may still be formed.

The temperature which may be employed in the oxygenate conversion process may vary over a wide range depending, at least in part, on the selected molecular sieve catalyst. In general, the process can be conducted at an effective temperature between about 200° C. (392° F.) and about 700° C. (1292° F.). Temperatures outside the stated range are not excluded, although they do not fall within certain desirable embodiments of the present invention. At the lower end of the temperature range, and thus, generally at a lower rate of reaction, the formation of the desired light olefin products may become markedly slow. At the upper end of the temperature range and beyond, the oxygenate conversion process may not form an optimum mount of light olefin products. Notwithstanding these factors, the reaction will still occur and the feedstock, at least in part, can be converted to the desired light olefin products at temperatures outside the range between about 200° C. (392° F.) and about 700° C. (1292° F.).

The selection of a particular catalyst for use in the oxygenate conversion process depends upon the particular oxygenate conversion process and other factors known to those skilled in the art which need not be further discussed herein. In a preferred aspect of the present invention where an aliphatic hetero compounds are converted into light olefins, it is preferred that the catalysts have relatively small pores. The preferred small pore catalysts are defined as having pores at least a portion, preferably a major portion, of which have an average effective diameter characterized such that the adsorption capacity (as measured by the standard McBain-Bakr gravimetric adsorption method using given adsorbate molecules) shows adsorption of oxygen (average kinetic diameter of about 0.346 nm) and negligible adsorption of isobutane (average kinetic diameter of about 0.5 nm). More preferably the average effective diameter is characterized by adsorption of xenon (average kinetic diameter of about 0.4 nm) and negligible adsorption of isobutane and most preferably by adsorption of n-hexane (average kinetic diameter of about 0.43 nm) and negligible adsorption of isobutane. Negligible adsorption of a given adsorbate is adsorption of less than three percent by weight of the catalyst and adsorption of the adsorbate is over three percent by weight of the adsorbate based on the weight of the catalyst. Certain of the catalysts useful in the present invention have pores with an average effective diameter of less than 5 Angstroms. The average effective diameter of the pores of preferred catalysts is determined by measurements described in D. W. Breck, *ZEOLITE MOLECULAR SIEVES* by John Wiley & Sons, New York (1974), hereby incorporated by reference in its entirety. The term effective diameter is used to denote that occasionally the pores are irregularly shaped, e.g., elliptical, and thus the pore dimensions are characterized by the molecules that can be adsorbed rather than the actual dimensions. Preferably, the small pore catalysts have a substantially uniform pore structure, e.g., substantially uniformly sized and shaped pore. Suitable catalyst may be chosen from among layered clays, zeolitic molecular sieves, and non-zeolitic molecular sieves.

Zeolitic molecular sieves in the calcined form may be represented by the general formula:

$$Me_{2/n}O:Al_2O_3:xSiO_2:yH_2O$$

where Me is a cation, x has a value from about 2 to infinity, n is the cation valence and y has a value of from about 2 to 10.

Typically, well-known zeolites which may be used include chabazite—also referred to as Zeolite D, clinoptilolite, erionite, faujasite—also referred to as Zeolite X and Zeolite Y, ferrierite, mordenite, Zeolite A, Zeolite P, ZSM-5, ZSM-11, and MCM-22. Other zeolites include those having a high silica content, i.e., those having silica to alumina ratios greater than 10 and typically greater than 100 can also be used. One such high silica zeolite is silicalite, as the term used herein includes both the silicapolymorph disclosed in U.S. Pat. No. 4,061,724 and also the F-silicate disclosed in U.S. Pat. No. 4,073,865, hereby incorporated by reference. Detailed descriptions of some of the above identified zeolites may be found in D. W. Breck, supra.

Non-zeolitic molecular sieves include molecular sieves which have the proper effective pore size and are embraced by an empirical chemical composition, on an anhydrous basis, expressed by the empirical formula:

$$(EL_xAl_yP_z)O_2$$

where EL is a metal selected from the group consisting of silicon, magnesium, zinc, iron, cobalt, nickel, manganese, chromium and mixtures thereof, x is the mole fraction of EL and is at least 0.005, y is the mole fraction of Al and is at least 0.01, z is the mole fraction of P and is at least 0.01 and x+y+z=1. When EL is a mixture of metals, x represents the total amount of the metal mixture present. Preferred metals (EL) are silicon, magnesium and cobalt with silicon being especially preferred.

The preparation of various ELAPOs are well known in the art and may be found in U.S. Pat. Nos. 5,191,141 (ELAPO); 4,554,143 (FeAPO); 4,440,871 (SAPO); 4,853,197 (MAPO, MnAPO, ZnAPO, CoAPO); 4,793,984 (CAPO), 4,752,651 and 4,310,440 all of which are incorporated by reference. Generally, the ELAPO molecular sieves are synthesized by hydrothermal crystallization from a reaction mixture containing reactive sources of EL, aluminum, phosphorus and a templating agent. Reactive sources of EL are the metal salts such as the chloride and nitrate salts. When EL is silicon, a preferred source is fumed, colloidal or precipitated silica. Preferred reactive sources of aluminum and phosphorus are pseudo-boehmite alumina and phosphoric acid. Preferred templating agents are amines and quaternary ammonium compounds. An especially preferred templating agent is tetraethylammonium hydroxide (TEAOH). The reaction mixture is placed in a sealed pressure vessel, optionally lined with an inert plastic material such as polytetrafluoroethylene and heated preferably under autogenous pressure at a temperature between about 50° C. and 250° C. and preferably between about 100° C. and 200° C. for a time sufficient to produce crystals of the ELAPO molecular sieve. Typically the time varies from about 2 hours to about 30 days and preferably from about 4 hours to about 20 days. The desired product is recovered by any convenient method such as centrifugation or filtration. It is known that the particle size of the ELAPO molecular sieve can be reduced by stirring the reaction mixture at high speeds (see examples) and by using TEAOH as the templating agent. It is preferred that the ELAPO molecular sieves are composed of particles at least 50% of which have a particle size less than 1.0 µm and no more than 10% of the ELAPO particles have a particle size greater than 2.0 µm. The ELAPOs which are synthesized using the process described above will usually contain some of the organic templating agent in its pores. In order for the ELAPOs to be active catalyst, the templating agent in the pores must be removed by heating the ELAPO powder in an oxygen containing atmosphere at a temperature of about 200° C. to about 700° C. until the template is removed, usually a few hours. A preferred embodiment of the invention is one in which the metal (EL) content varies from about 0.005 to about 0.05 mole fraction. If EL is more than one metal, then the total concentration of all the metals is between about 0.005 and 0.05 mole fraction. An especially preferred embodiment is one in which EL is silicon (usually referred to as SAPO). The SAPOs which can be used in the instant invention are any of those described in U.S. Pat. Nos. 4,440,871; 5,126,308, and 5,191,141. Of the specific crystallographic structures described in the '871 patent, the SAPO-34, i.e., structure type 34, is preferred. The SAPO-34 structure is characterized in that it adsorbs xenon but does not adsorb isobutane, indicating that it has a pore opening of about 4.2 Å. Another SAPO, SAPO-17, as exemplified in Examples 25 and 26 of the '871 patent, is also preferred. The SAPO-17 structure is characterized in that it adsorbs oxygen, hexane, and water but does not adsorb isobutane, indicating that it has a pore opening of greater than about 4.3 Å and less than about 5.0 Å.

The preferred catalyst for the oxygenate conversion zone may be, and preferably is, incorporated into solid particles in which the catalyst is present in an amount effective to promote the desired hydrocarbon conversion. In one aspect, the solid particles comprise a catalytically effective amount of the catalyst and at least one matrix material, preferably selected from the group consisting of binder materials, filler materials, and mixtures thereof to provide a desired property or properties, e.g., desired catalyst dilution, mechanical strength, and the like to the solid particles. Such matrix materials are often, to some extent, porous in nature and may or may not be effective to promote the desired hydrocarbon conversion. The matrix materials may promote conversion of the feedstream and often provide reduced selectivity to the desired product or products relative to the catalyst. Filler and binder materials include, for example, synthetic and naturally occurring substances such as metal oxides, clays, silicas, alms, silica-aluminas, silica-magnesias, silica-zirconias, silica-thorias, silica-berylias, silica-titanias, silica-alumina-thorias, silica-alumina-zirconias, aluminophosphates, mixtures of these and the like. If matrix materials, e.g., binder and/or filler materials, are included in the catalyst composition, the non-zeolitic and/or zeolitic molecular sieves preferably comprise about 1% to 99%, more preferably about 5% to about 90% and still more preferably about 10% to about 80%, by weight of the total composition. The preparation of solid particles comprising catalyst and matrix materials is conventional and well known in the art and, therefore, need not be discussed in detail herein.

During the oxygenate conversion reaction, a carbonaceous material, i.e., coke is deposited on the catalyst. The carbonaceous deposit material has the effect of reducing the number of active sites on the catalyst which thereby affects the extent of the conversion. During the conversion process a portion of the coked catalyst is withdrawn from the reaction zone and regenerated to remove at least a portion of the carbonaceous material. Preferably, the carbonaceous material is removed from the catalyst by oxidative regeneration wherein the catalyst which is withdrawn from the reactor is contacted with an oxygen-containing gas at sufficient temperature and oxygen concentration to allow the desired mount of the carbonaceous materials to be removed from the catalyst.

Depending upon the particular catalyst and conversion, it can be desirable to substantially remove the carbonaceous material e.g., to less than 1 wt %, or only partially regenerate the catalyst, e.g., to from about 2 to 30 wt % carbon. Preferably, the regenerated catalyst will contain about 0 to 20% and more preferably from about 0 to 10% carbon. Additionally, during regeneration there can be oxidation of sulfur and in some instances nitrogen compounds along with the removal of metal materials from the catalyst. Moreover, regeneration conditions can be varied depending upon catalyst used and the type of contaminant material present upon the catalyst prior to its regeneration.

The processes of this invention also include, in addition to the hydrocarbon conversion, and carbon burn-off, or regeneration steps, further treatment steps such as, for example, the subsequent sulfiding of the regenerated catalyst to slightly temper its activity when such treatment is required. Such tempering substantially, if not totally, reduces the initial high activity present if the catalyst is not sulfided thereby preventing high rates of degradation in yields. Many processes utilize catalysts which contain metals which must be treated, such as by sulfiding, in order to temper the activity of the catalyst to prevent runaways of low quality yields or high coking rates upon the catalyst. Specifically, such processes which typically require sulfiding are reforming and the hydroprocessing process, although other processes may be utilized which initial catalyst activity is desired to be substantially tempered by a sulfiding step.

When the synthesis gas production zone employs a primary reformer to convert the hydrocarbon feed to the carbon oxide/hydrogen mixture, a significant amount of treated water is required for the reaction. In the process of the present invention, a significant portion and preferably essentially all of the water required by the synthesis gas production zone may be supplied by the water produced in the oxygenate conversion zone, or MTO zone. It was determined that the syngas production zone water requirement is slightly less than the amount of water produced from an MTO zone, based on the conversion of methanol to light olefins. Thus, the direct transfer of that by-product water produced in the MTO zone to the syngas production zone, without further treatment to remove hydrocarbons or oxygenates, results in significant capital and operating cost savings. When the synthesis gas production zone above employs both primary reforming and secondary reforming, wherein oxygen is employed, the overall water requirement for the reforming zone is reduced. In this operation, all of the make up water for the primary reforming stage may be supplied by the water produced in the MTO zone. In addition, excess water from the MTO zone may be passed to an etherification zone for the production of diisopropyl ether (DIPE) by etherification of propylene with a portion of the excess water from the MTO zone. Since the DIPE process does not require a high purity propylene feed, the de-ethanizer in the MTO fractionation zone may be eliminated.

DETAILED DESCRIPTION OF THE DRAWINGS

The process of the present invention is hereinafter described with reference to the figures which illustrate various aspects of the process. It is to be understood that no limitation to the scope of the claims which follow is intended by the following description. Those skilled in the art will recognize that these process flow diagrams have been simplified by the elimination of many necessary pieces of process equipment including some heat exchangers, process control systems, pumps, fractionation systems, etc. It may also be discerned that the process flow depicted in the figures may be modified in many aspects without departing from the basic overall concept of the invention.

Figure 1:
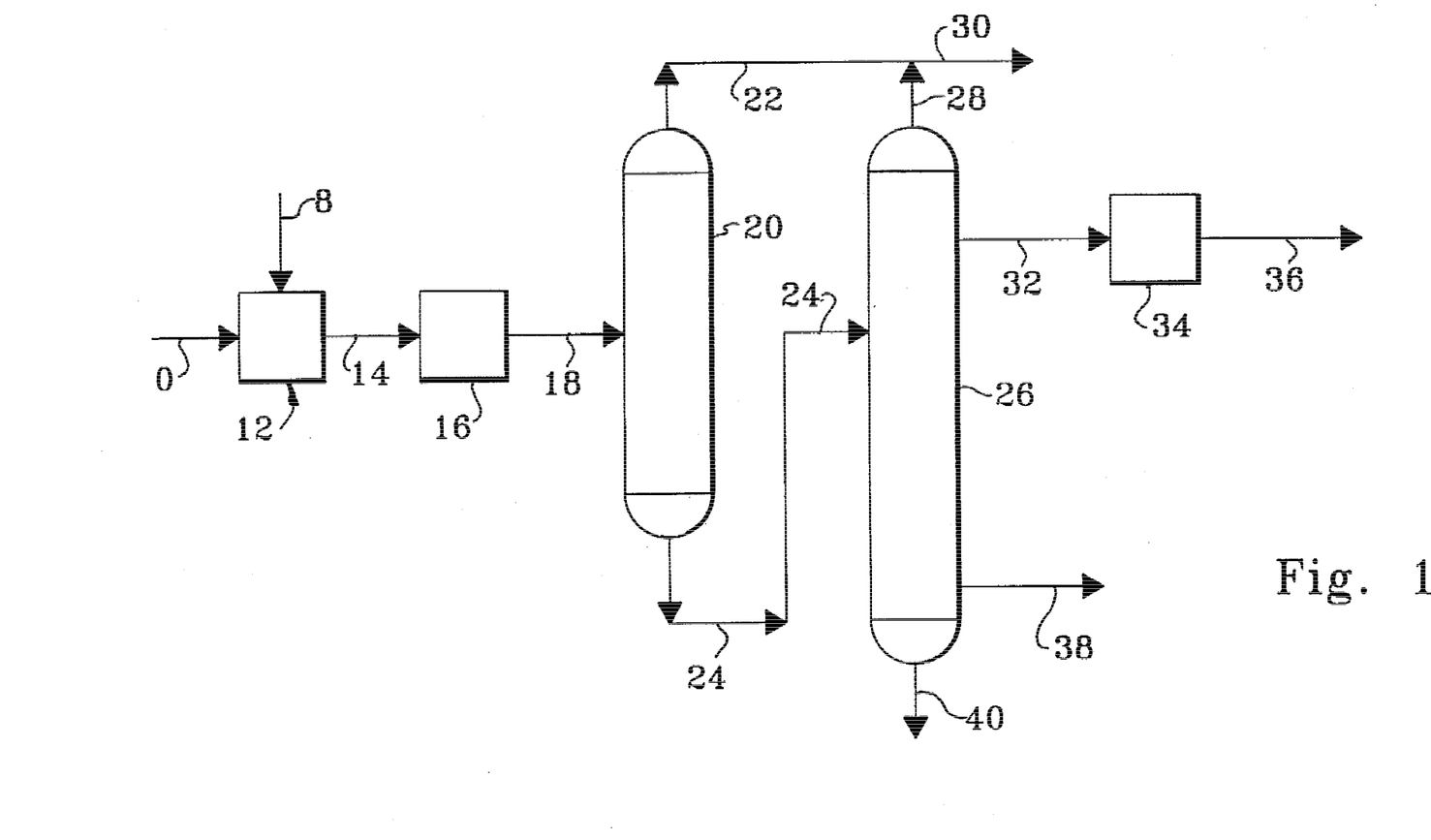
FIG. 1 is a schematic process flow diagram illustrating the prior art process.

With reference to FIG. 1 which shows the prior art process flow, a hydrocarbon gas feedstream 10 and a water stream 8 are passed to a syngas production zone 12 to produce a synthesis gas stream 14. The syngas production zone 12, or synthesis gas plant, conventionally operates at a reaction temperature ranging from about 800° C.–950° C., a pressure ranging from about 10–30 bar, and a water to carbon molar ratio ranging from about 2.0 to about 3.5. In the syngas production zone 12, impurities such as sulfur compounds, nitrogen compounds, particulate matter, and condensibles are removed in the conventional manner to provide the synthesis gas stream 14 reduced in contaminants and containing a molar ratio of hydrogen to carbon oxide (carbon monoxide plus carbon dioxide) ranging from about 2 to about 3, and more typically the molar ratio of hydrogen to carbon oxide varies from about 2.0 to about 2.3. Optionally (not shown), this ratio may be varied according to the carbon monoxide shift reaction:

$$CO + H_2O \rightleftharpoons CO_2 + H_2$$

over a copper/zinc or chromium oxide catalyst in the conventional manner. The synthesis gas stream is removed from the synthesis gas plant via line 14. The synthesis gas stream 14 is passed to a carbon oxide conversion zone 16. In the carbon oxide conversion zone 16, the synthesis gas will undergo conversion to form reduction products of carbon oxides, such as alcohols, at conditions including a reactor temperature ranging from about 150° C. (300° F.) to about 450° C. (850° F.) at a pressure ranging from about 1 to about 1000 atmospheres over a variety of catalysts. Catalysts based on ZnO for the production of methanol and dimethyl ether are preferred. A crude oxygenate stream comprising methanol, dimethyl ether, fusel oils, and water is withdrawn from the carbon oxide conversion zone 16 in line 18. The fusel oil includes heavier alcohols. The crude oxygenate stream is passed to a topping column 20 which operates at about 60 kPa (0.6 atm) to remove a first light ends stream 22 comprising dissolved gases—such as hydrogen, methane, carbon oxides, and nitrogen, and light ends—such as ethers, ketones, and aldehydes. The topping column bottoms 24 are removed from the topping column 20 and passed to a refining column 26. In the refining column 26, a second light ends stream 28 is withdrawn from the top of the refining column 26 and combined with the first light ends stream 22 to form a combined purge stream 30. The combined purge stream is typically used for fuel. The refining column 26 operating at about atmospheric pressure further separates methanol from the water and fusel oils to provide a high purity methanol stream 32, a fusel oil stream 38 and a second water stream 40. At least a portion of the high purity methanol stream 32 is passed via lines 32 to an oxygenate conversion zone 34 to produce an effluent stream 36 comprising light olefins having from 2 to 4 carbon atoms per molecule and water. The oxygenate conversion zone is maintained at a reaction temperature ranging from about 350° C. to about 525° C. and a pressure of about 1 to about 5 atmospheres. The oxygenate conversion reaction zone contains a molecular sieve catalyst, and preferably contains a metal aluminophosphate catalyst such as a SAPO catalyst for the conversion of at least a portion of the oxygenate product stream into $C_2$–$C_4$ olefins. The oxygenate product stream in line 32 is introduced to the oxygenate conversion reaction zone 34 containing a fluidized bed of the molecular sieve catalyst in the presence of a diluent such as steam or other inert material. The effluent stream 36 is separated by conventional methods into olefin products including ethylene, propylene, and butylene (not shown).

Figure 2:
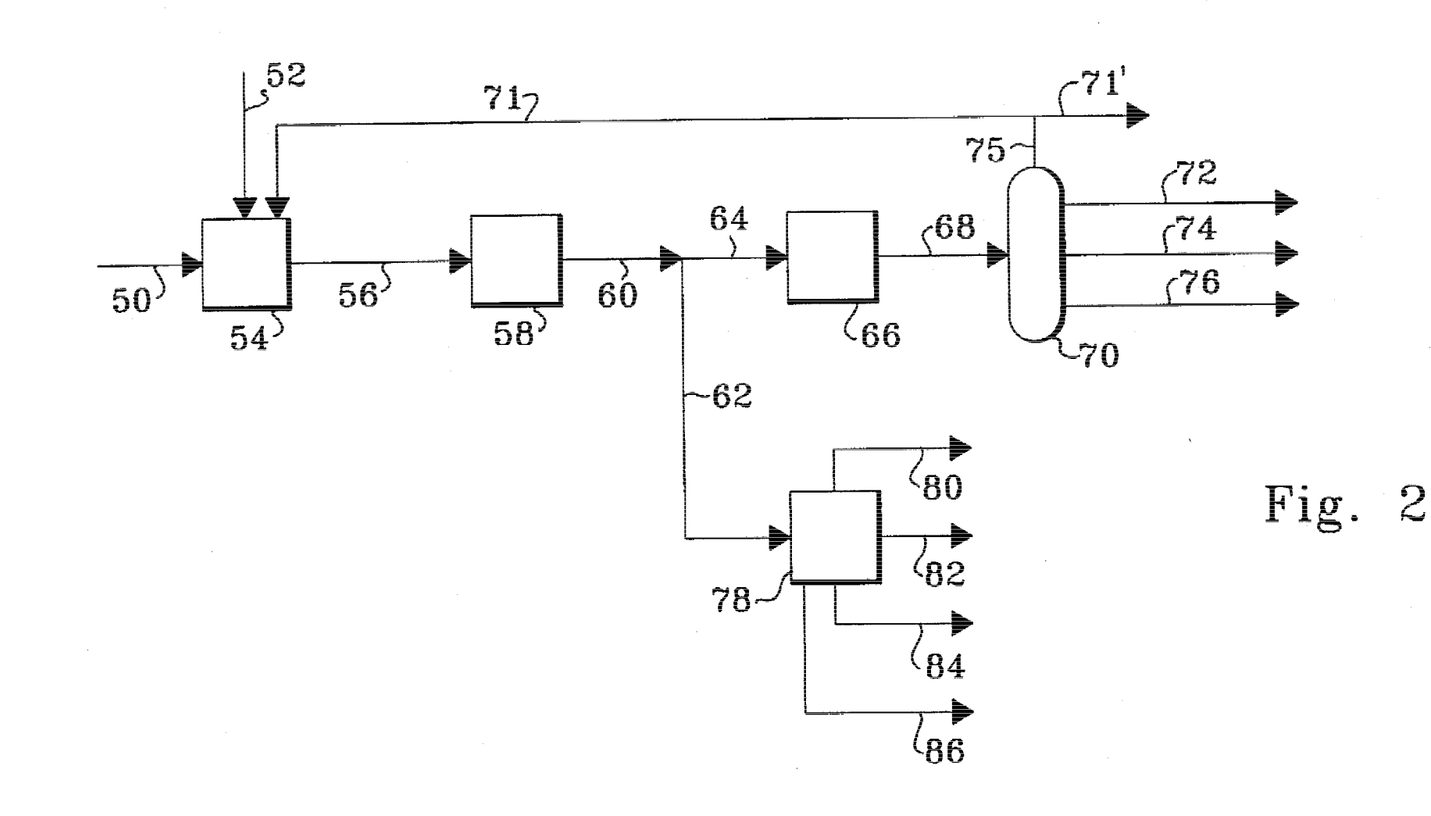
FIG. 2 is a schematic process flow diagram illustrating the passing of crude methanol to an oxygenate conversion zone of the instant invention.

With reference to FIG. 2 illustrating the process of the present invention, a hydrocarbon gas feedstream 50 is passed to a syngas production zone 54 with a water recycle stream 71 to produce a synthesis gas stream 56. The syngas production zone 54 operates in the manner described hereinabove with respect to the syngas production zone 12 of FIG. 1. The synthesis gas stream 56 is passed to a carbon oxide conversion zone 58 as described hereinabove with respect to the carbon oxide conversion zone 16 of FIG. 1 to provide a crude oxygenate or crude methanol stream 60. At least a portion of the crude methanol stream 60 is passed via line 64 to an oxygenate conversion zone 66. The oxygenate conversion zone 66 operates in the manner described hereinabove with respect to the oxygenate conversion zone 34 of FIG. 1 and an effluent stream 68 comprising water and light olefins having 2 to 4 carbon atoms per molecule is withdrawn from the oxygenate conversion zone 66 and passed to a separation zone 70 where the light olefins are separated by conventional means into the by-product water stream 75, an ethylene product 72, a propylene product 74 and a butylene product 76. At least a portion of the by-product water stream is returned to the syngas production zone 54 to provide a portion of the water recycle stream 71 and a portion is withdrawn as a drag stream in line 71' to prevent the build-up of impurities in the process. The drag stream 71', at a much reduced flow rate, is passed to conventional water treatment (not shown). Thus, by passing at least a portion of the crude methanol stream 60 to the olefin product zone 66 and recycling at least a portion of the by-product water, a significant capital cost and operating cost savings can be achieved substantially reducing or eliminating the fractionation of the crude methanol to remove the light ends, fusel oils and water. A remaining portion of the crude methanol stream 60 may be passed via lines 60 and 62 to a conventional crude methanol fractionation zone 78 comprising a topping column and a refining column as described with respect to FIG. 1 to provide a purge stream 80 for fuel, a high purity methanol stream 82, a fusel oil stream 84, and a water stream 86. Any light ends such as ethers, ketones, and aldehydes present in the oxygenate conversion zone will react to produce additional amounts of olefins such as ethylene. The presence of light gases such as $CO_2$ and methane provide additional diluent required by the oxygenate conversion zone to improve the selectivity of the oxygenate conversion catalyst to produce the light olefin products. The fusel oils, comprising heavier alcohols, in the crude methanol react in the olefin production zone 66 to form additional ethylene, propylene and butylene, further enhancing the yields of desired products. The water in the crude methanol stream serves as the diluent for the olefin production reaction and eliminates the need to separately treat and add makeup water to the olefin production zone.

In the operation of the carbon oxide conversion zone 58, as the reaction proceeds, the yield and selectivity to methanol will decline as the catalyst ages with the associated increase in the production of ethers and fusel oils.

Figure 3:
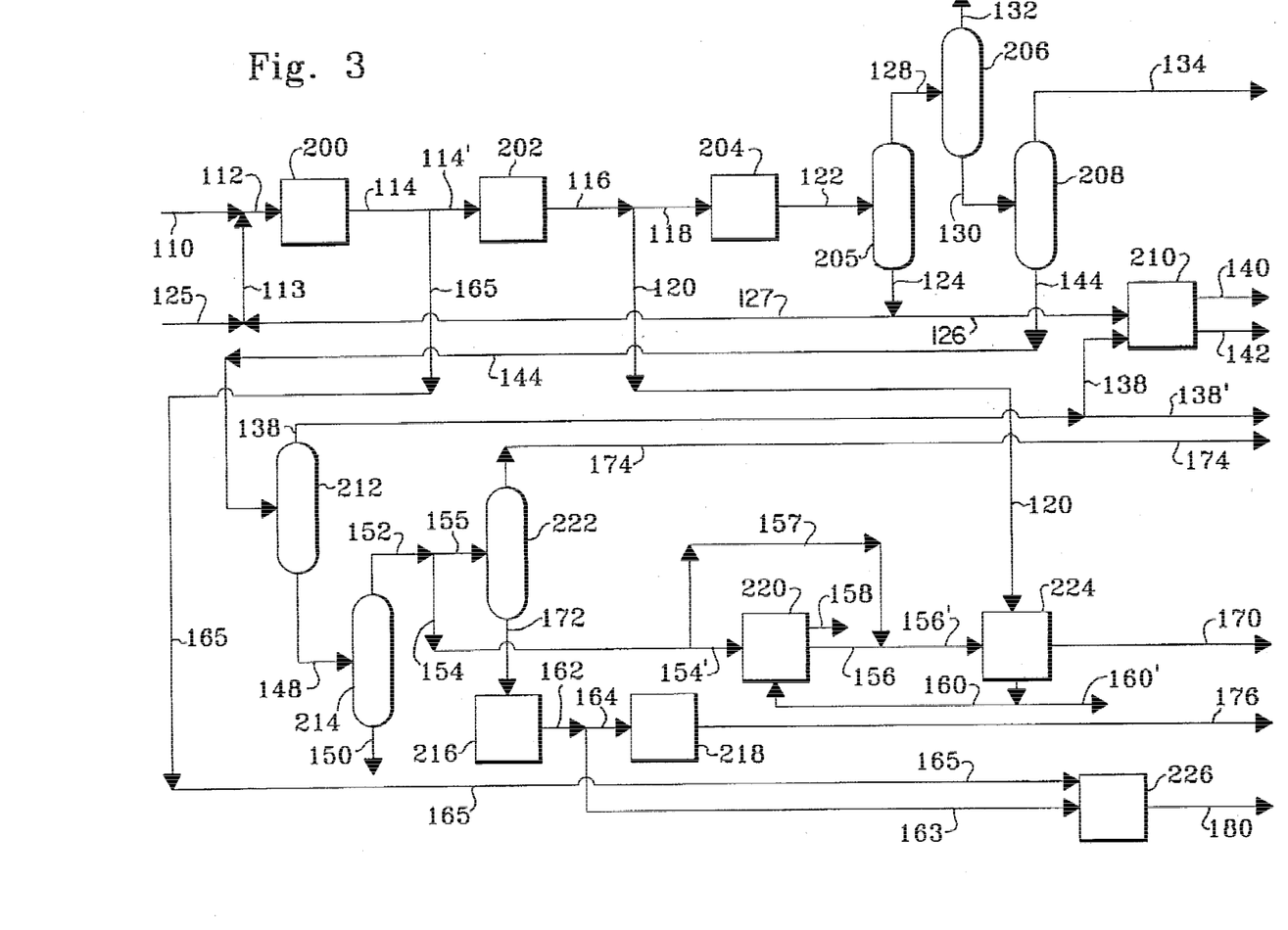
FIG. 3 is a schematic flow diagram of the process of the present invention illustrating the integration of a petrochemical complex with water recycle.

With reference to FIG. 3, a hydrocarbon gas feedstream 110 is combined with a water stream 113 and the combination is passed via line 112 to a syngas production zone 200 to produce a synthesis gas stream 114. The syngas production zone 200, or synthesis gas plant, conventionally operates at a reaction temperature ranging from about 800° C.–950° C., a pressure ranging from about 10–30 bar, and a water to carbon molar ratio ranging from about 2.0 to about 3.5. In the syngas production zone 200, impurities such as sulfur compounds, nitrogen compounds, particulate matter, and condensibles are removed in the conventional manner to provide the synthesis gas stream 114 reduced in contaminants and containing a molar ratio of hydrogen to carbon oxide (carbon monoxide plus carbon dioxide) ranging from about 2 to about 3, and more typically the molar ratio of hydrogen to carbon oxide varies from about 2.0 to about 2.3. Optionally (not shown), this ratio may be varied according to the carbon monoxide shift reaction:

$$CO + H_2 \rightleftharpoons CO_2 + H_2$$

over a copper/zinc oxide or chromium catalyst in the conventional manner. The synthesis gas stream is removed from the synthesis gas plant via lines 114 and 114'. The synthesis gas stream 114' is passed to a carbon oxide conversion zone 202. In the carbon oxide conversion zone 202, Catalysts based on ZnO for the production of methanol and dimethyl ether are preferred. An oxygenate product stream comprising methanol and/or dimethyl ether is withdrawn from the carbon oxide conversion zone 202 in line 116. At least a portion of the oxygenate product stream 116 is passed via lines 116 and 118 to an olefin production zone 204 to produce an effluent stream 122 comprising light olefins having from 2 to 4 carbon atoms per molecule and water. The oxygen conversion reaction zone is maintained at a reaction temperature ranging from about 350° C. to about 525° C. and a pressure of about 1 to about 5 atmospheres. The oxygenate conversion reaction zone contains a molecular sieve catalyst, and preferably contains a metal aluminophosphate catalyst such as a SAPO catalyst for the conversion of at least a portion of the oxygenate product stream into $C_2$–$C_4$ olefins. The oxygenate product stream in line 118 is introduced to the reaction zone containing a fluidized bed of the molecular sieve catalyst in the presence of a diluent such as steam or other inert material. The effluent stream 122 is passed to a water separation zone 205 to separate the hydrocarbon phase from the water phase thereby producing a light hydrocarbon stream 128 comprising olefins and a second water stream 124. At least a portion of the second water stream in line 124 is passed to line 127 where it is admixed with a make-up water stream in line 125 to form the water stream in line 113. Thus, at least a portion of the second water stream 124 and the make-up water stream 125 provide a water admixture and which is passed to the syngas production zone 200 to provide the water stream 113. The light hydrocarbon stream 128 is passed to a de-methanizer zone 206 to provide a methane stream 132 which may be employed for fuel, and a $C_2^+$ stream 130. The $C_2^+$ stream 130 is passed to an ethylene fractionation zone 208 to produce an ethylene product stream in line 134 and a net bottom stream or $C_3^+$ stream in line 144. The $C_3^+$ stream 144 is passed to a $C_3/C_4$ fractionation zone 212 wherein the hydrocarbons are separated into a crude propylene stream comprising propylene, propane, and ethane in line 138 and a $C_4^+$ stream comprising butenes in line 148. A portion of the crude propylene stream may be withdrawn as a crude propylene product in line 138'. Preferably, the crude propylene stream comprises at least about 90 vol-% propylene, more preferably the crude propylene stream comprises more than about 95 vol-% propylene, and most preferably the crude propylene stream comprises from about 92 to about 96 vol-% propylene. A portion of the crude propylene stream 138 is passed to a first etherification zone 210 to produce diisopropyl ether, DIPE. In the first etherification zone 210, a portion of the second water stream 126 is reacted with the crude propylene stream 138 over a resin catalyst to provide a first ether product 142 comprising diisopropyl ether and a first light end stream 140 comprising ethane and propane. The first ether product is withdrawn in line 142 to be used for gasoline blending and the first light ends stream comprising essentially saturates is withdrawn in line 140. The first light ends stream 140 may be used to provide fuel to the complex or sold as liquified petroleum gas. When it is desired to recover a portion of the propylene in the crude propylene stream 138 at high purity, a portion of the crude propylene stream 138' is passed to a propylene fractionation zone (not shown) to produce a high purity propylene stream and a net overhead stream comprising propylene and propane. The net overhead stream is returned to the first etherification zone 210 for the conversion of the remaining propylene to the first ether product, DIPE.

The $C_4^+$ stream 148, is withdrawn from the $C_3/C_4$ fractionation zone 212 and passed to a butylene fractionation zone 214. In the butylene fractionation zone 214, the butylenes are separated from the $C_5$ and heavier hydrocarbons 150. A primary butylene stream 152 and a $C_5$ and heavier stream 150 are withdrawn from the butylene fractionation zone 214. Depending upon the selectivity of the catalyst in the olefin production zone 204, the primary butylene stream 152 will contain at least some isobutylene as well as other isomers of butene, including butene-1, 2-cis-butene, and 2-trans-butene. The primary butylene stream 152 is passed to a butene separation zone 222 via lines 152 and 155 to provide a butene-1 stream 174 and a secondary butene stream 172. The butene-1 stream 174 is withdrawn as a butene-1 product stream 174 and, although not shown in the drawing, may be used as a copolymer with ethylene to produce linear low density polyethylene. Preferably, the butene-1 product stream comprises greater than about 97 mol-% butene-1, and most preferably the butene-1 product comprises about 99.5 mole percent butene-1. When the butene-1 stream 174 comprises greater than about 40 mol-% isobutene, the butene-1 stream may be polymerized to produce a poly isobutylene stream (not shown).

In one alternative, the secondary butene stream 172 comprising n-butenes is passed to a dimerization zone 216 to form a dimerized stream 162 and a portion of the dimerized stream 162 is hydrogenated by passing the dimerized stream in lines 162 and 164 to a hydrogenation zone 218 to produce a $C_8$ alkylate 176 having a high octane for use in blending motor gasoline. When it is desired to produce $C_8$ dimer to make nonyl alcohols 180, a portion of the $C_8$ dimer may be withdrawn from the dimerization zone 216 and passed via lines 162, and 163 to an hydration zone 226 wherein the dimer is reacted at conventional hydroformylation conditions in the presence of synthesis gas 165 withdrawn as a portion of the synthesis gas stream 114 to produce a nonyl alcohol stream 180. The hydroformylation reaction takes place over a hydroformylation catalyst comprising carbonyls of Group VIII transition metals such as $Co_2(CO)_8$ and $RhH(CO)(PPh_3)_3$ at temperatures ranging from about 50° C. to about 250° C., hydrogen to carbon monoxide molar ratios ranging from about 1:1 to about 100:1, and total pressures ranging from 1 to about 300 atmospheres. Operating conditions and catalyst compositions for the hydroformylation reaction is disclosed in U.S. Pat. Nos. 5,087,763 and 4,219,684 and an article rifled "Hydroformylation of Olefins Using Rodium Complex", by Yamshi Matsui et al., *Bulletin of the Japan Petroleum Institute*, Vol. 19, No. 1, May 1977, pages 62–67, and hereby incorporated by reference. Nonyl alcohols are useful as plasticizers in the manufacture of polyethylene and polypropylene polymers.

In another alternative flow scheme, the primary butylene stream 152 is passed to an isomerization zone 220 via lines 154 and 154' to produce an isomerate stream 156 comprising isobutene and a third light ends stream 158. The isomerate stream 156 is passed via lines 156 and 156' to a second etherification zone 224 wherein a portion of the oxygenate product stream 116 from the carbon oxide conversion 202 is passed via lines 116 and 120 to the second etherification zone 224 where it is reacted with the isomerate stream 156' to produce a second ether stream 170 having a high octane number, and an unreacted $C_4$ stream 160. At least a portion of the unreacted $C_4$ stream in line 160 may be returned to the isomerization zone 220 via line 160 where for further conversion. A portion of the unreacted $C_4$ stream 160 is withdrawn in line 160' as a purge stream to be used for fuel or blended into gasoline.

Although not shown in drawing, a portion of butene-1 produced from the fractionation zone 222 in line 174 may be polymerized with a portion of the ethylene product stream in line 134 in a polyethylene zone to produce a linear low density polyethylene product.

The following examples are only used to illustrate the present invention and are not meant to be limiting.

EXAMPLES

Example I

According to the conventional carbon oxide conversion separation scheme as shown in the FIG. 1 for the production of light olefins from natural gas, about 173 MKg/hr of a natural gas stream and about 242 MKg/hr of a water stream are converted into methanol in the conventional manner with a single stage of primary reforming to produce a synthesis gas followed by the conversion of the synthesis gas to methanol and the separation of the crude methanol into high purity methanol. Table 1 summarizes the overall material balance in Kg/hr for these two conversion units. Referring to Table 1, a portion of the unconverted natural gas comprising hydrogen is withdrawn as a purge stream (3) to provide fuel gas for the reformer. Approximately 289 MKg/hr of pure methanol (8) is produced. In the conventional process for producing pure methanol, the crude methanol(4) is fractionated a first time to remove a light purge stream(5) comprising carbon dioxide and dimethyl ether, fractionated a second time to remove heavy alcohols such as isopropanol as a heavy purge (6), and fractionated a third time to remove waste water stream(7). The high purity methanol product(8) is passed an olefin production zone, or MTO conversion zone. In the oxygenate conversion zone, the high purity methanol is converted into light olefins and water. Table 2 shows the material balance for the conversion of high purity methanol to light olefins. The reactor effluent is treated with a caustic wash to remove entrained catalyst (not shown) and the caustic washed effluent is cooled and flashed to remove water. From the 288 MKg/hr of pure methanol feed to the reactor, about 235 MKg/hr of excess water are produced, along with 62.4 MKg/hr of ethylene, 38.8 MKg/hr of propylene and about 15.2 MKg/hr of butylenes.

Example II

According to the process of the present invention as illustrated in FIG. 2, the natural gas stream 50 and water 52 are charged to the syngas plant 54 in the same amounts as in Example I. The synthesis gas 56 produced in the syngas plant is passed to a methanol plant 58 to convert the synthesis gas to crude methanol 60. The amount of crude methanol 60 produced is shown in Table 3. A smaller purge stream (AA) relative to Example I, is removed as reformer feed. The additional amounts of $H_2$—$C_1$ and CO2 present in the feed to the oxygenate conversion do not harm the oxygenate conversion reaction, and in fact act as diluents. DME remaining in the crude methanol is converted to light olefins. The crude methanol(AB), comprising light ends, water, and fusel oil is charged to the oxygenate conversion zone 66 to produce the reactor effluent shown in Table 3. Comparing the reactor effluent(3) shown in Table 2 as produced in Example I from high purity methanol, to the reactor effluent(AC) shown in Table 3 as produced from crude methanol, it can be seen that the ethylene yield has increased by about 0.7 wt-%. The overall production of light olefins is shown in columns AH–AL in Table 3. In addition, no make-up water was required in the oxygenate conversion zone, significantly reducing the operating costs of the methanol plant by eliminating the separation of the water and by eliminating the make-up water treatment facilities in the oxygenate conversion zone.

Example III

The value of the additional production of light olefins from crude methanol as described in Example II relative to the amount of light olefins produced in Example I, is shown in Table 4. Although the total amount of the ethylene produced from crude methanol is about 0.7 wt-%, the value of the additional ethylene production at current market prices is about 2 million dollars per year. The additional amount of propylene, olefins and butylenes that is produced from crude methanol amounts to a total value of about three million dollars per year, in addition to the savings from the elimination of the methanol purification steps.

TABLE 1

NATURAL GAS TO METHANOL
CONVENTIONAL STEAM REFORMING PROCESS
KILOGRAMS PER HOUR

| COMP. | 1 NAT FEED | 2 MAKE UP WATER | 3 PURGE TO FG | 4 CRUDE MeOH | 5 LIGHT PURGE | 6 HEAVY PURGE | 7 WASTE WATER | 8 HP MEOH |
|---|---|---|---|---|---|---|---|---|
| CH4 | 135797 | | 21840 | 113 | 113 | | | |
| CO2 | 2945 | | 6570 | 1790 | 1790 | | | |
| CO | 91 | | 3670 | | | | | |
| H2 | 407 | | 17536 | | | | | |
| C2H8 | 20866 | | | | | | | |
| C3+ | 13254 | | | | | | | |
| DME | | | | 136 | 136 | 136 | | |
| Hv. Alc | | | | | 136 | 136 | | |
| CH3OH | | | 2266 | 288517 | 22 | 22 | 68 | 288404 |
| H2O | 00 | 242278 | 226 | 72701 | 00 | 0 | 72475 | 226 |
| TOTAL | 173360 | 242478 | 52244 | 363394 | 2061 | 158 | 72543 | 288630 |

TABLE 2

METHANOL TO OLEFINS (MTO) MATERIAL BALANCE
HIGH PURITY METHANOL, KILOGRAMS PER HOUR

| COMP. | A<br>CH3OH<br>TO Rx | B<br>MAKE-UP<br>WATER | C<br>Rx. EFF | D<br>H2-C1 | E<br>COKE | F<br>WATER | G<br>CAUSTIC<br>WASH |
|---|---|---|---|---|---|---|---|
| H2-C1 | | | 3258 | 3250 | | | |
| CO2 | | | 622 | | | | 622 |
| C2= | | | 63041 | 309 | | | |
| C2H6 | | | 631 | 1 | | | |
| C3= | | | 39085 | | | | |
| C3H8 | | | 686 | | | | |
| C4+ | | | 15130 | | | | |
| H2O | 226 | 72500 | 234358 | | | 234359 | |
| CH3OH | 288404 | | 537 | | | 537 | |
| DME | | | | | | | |
| Hv Alc | | | | | | | |
| COKE | 000 | | 3782 | | 3782 | | |
| TOTAL | 288630 | 72500 | 361130 | 3560 | 3782 | 234896 | 622 |

| COMP. | H<br>C2= PROD | I<br>C3= PROD | J<br>C2 SAT | K<br>C3 SAT | L<br>C4+ PROD |
|---|---|---|---|---|---|
| CH4 | 8 | | | | |
| C2= | 62384 | 10 | 324 | | |
| C2H6 | 8 | 13 | 610 | | |
| C3= | | 38700 | 153 | 154 | 78 |
| C3H8 | | 91 | 16 | 547 | 31 |
| C4+ | | | | 63 | 15067 |
| TOTAL | 62400 | 38814 | 1103 | 764 | 15176 |

TABLE 3

CRUDE METHANOL TO OLEFINS (MTO) MATERIAL BALANCE
CRUDE METHANOL, KILOGRAMS PER HOUR

| COMP. | AA<br>PURGE<br>TO FG | AB<br>CRUDE<br>MeOH | AC<br>Rx. EFF | AD<br>H2-C1 | AE<br>COKE | AF<br>WATER | AG<br>CAUSTIC<br>WASH |
|---|---|---|---|---|---|---|---|
| H2-C$_1$ | 21540 | 413 | 3678 | 3670 | | | |
| CO$_2$ | 6170 | 2190 | 2820 | | | | 2820 |
| C$_2$= | | | 63471 | 311 | | | |
| C$_2$H$_6$ | | | 640 | 1 | | | |
| C$_3$= | | | 39293 | | | | |
| C$_3$H$_8$ | | | 690 | | | | |
| C$_4$+ | | | 15213 | | | | |
| H$_2$O | 201 | 72726 | 235226 | | | 235226 | |
| CH$_3$OH | 1066 | 289717 | 537 | | | 537 | |
| DME | 76 | 196 | | | | | |
| Hv Alc | | 136 | | | | | |
| COKE | 000 | | 3810 | | 3810 | | |
| TOTAL | 29053 | 365378 | 365378 | 3982 | 3810 | 235763 | 2820 |

| COMP. | AH<br>C2= PROD | AI<br>C3= PROD | AJ<br>C2 SAT | AK<br>C3 SAT | AL<br>C4+ PROD |
|---|---|---|---|---|---|
| CH4 | 8 | | | | |
| C2= | 62826 | 10 | 324 | | |
| C2H6 | 8 | 13 | 618 | | |
| C3= | | 38908 | 153 | 154 | 78 |
| C3H8 | | 91 | 16 | 552 | 31 |
| C4+ | | | | 63 | 15150 |
| TOTAL | 62842 | 39022 | 1111 | 769 | 15259 |

TABLE 4

**CRUDE METHANOL TO OLEFINS (MTO)
ADDITIONAL PRODUCT VALUE
CRUDE METHANOL, ANNUAL BASIS**

| PRODUCT: | PRODUCTION, Kg/HR | PRODUCTION, MTA | PRODUCT PRICE, $/MT | ADDED VALUE, MM$/Annum |
|---|---|---|---|---|
| Ethylene | 442 | 3536 | 600 | 2.12 |
| Propylene | 208 | 1664 | 500 | 0.83 |
| Butylene | 83 | 664 | 150 | 0.10 |
| TOTAL | 733 | 5864 | | 3.05 |

Example IV

According to the FIG. 3 stream 138' is a crude propylene stream which corresponds to the combination of the $C_3=$product, the $C_2$ saturates, and the $C_3$ saturates as (as shown in columns H, I, and J in Table 2). This represents the yield and composition of the crude propylene product. The crude propylene product comprises about 95 vol-% propylene and may be used without additional processing as chemical grade propylene.

Example V

As shown in Example I, the $C_4^+$ product stream (column L of Table 2) has the following composition:

| | $C_4^+$ Product, Kg/hr |
|---|---|
| $C_3H_6$ | 78 |
| $C_3H_8$ | 31 |
| $iC_4H_8$ | 380 |
| 1-n$C_4H_8$ | 3120 |
| 2-n$C_4H_8$ | 8440 |
| $C_4$-Saturates | 120 |
| $C_5$ Plus | 3007 |
| TOTAL | 15176 |

According to the FIG. 3, this is the composition of stream 155 which is passed to the butene separation zone 222 to provide a butene-1 stream 174 having a purity of about 90 wt-%.

Example VI

Further to Example I, the propylene stream in Table 2 (column I) will produce about 46.8 MKg/hr of diisopropylether (DIPE) when passed to the first etherification zone 210 as shown in the FIG. 3.

We claim:

1. A process for the production of light olefins from a hydrocarbon gas feedstream, comprising methane and ethane, said process comprising:
   a) passing said feedstream in combination with a water stream to a syngas production zone to produce a synthesis gas stream and passing said synthesis gas stream to a carbon oxide conversion zone to produce a crude oxygenate stream comprising methanol, dimethyl ether and fusel oil;
   b) passing at least a portion of the crude oxygenate stream in the presence of a diluent to an olefin production zone containing a small pore non-zeolitic catalyst having a pore size less than about 5 Angstroms to produce a light olefin stream consisting essentially of light olefins having 2 to 4 carbon atoms per molecule and water,
   c) passing said light olefin stream to a separation zone to provide a combined light olefin stream comprising ethylene, propylene, and butylene and a water by-product stream and returning at least a portion of said water by-product stream to provide said water stream and at least a portion of said diluent.

2. The process of claim 1 wherein said small pore non-zeolitic catalyst comprises a metal aluminophosphate molecular sieve having an empirical chemical composition on an anhydrous basis expressed by the following formula:

$$(EL_xAl_yP_z)O_2$$

wherein EL is a metal selected from the group consisting of silica, magnesium, zinc, iron, cobalt, nickel, manganese, chromium, and mixtures thereof, x is the mole fraction of EL and is at least 0.005, y is the mole fraction of Al and is at least 0.01, z is the mole fraction of P and is at least 0.01 and $x+y+z=1$.

3. The process of claim 2 wherein said metal aluminophosphate molecular sieve comprises a SAPO structure.

4. The process of claim 3 wherein said SAPO structure comprises a SAPO-34 structure.

5. The process of claim 3 wherein said SAPO structure comprises a SAPO-17 structure.

6. The process of claim 1 wherein said carbon oxide conversion zone comprises a methanol plant.

7. The process of claim 1 wherein said crude oxygenate stream comprises water.

8. A process for the production of light olefin from a hydrocarbon gas feedstream comprising methane and ethane, said process comprising:
   a) passing said feedstream in combination with a water stream to a syngas production zone to produce a synthesis gas stream comprising hydrogen and a carbon oxide and passing said synthesis gas stream to a methanol plant to produce a crude methanol stream comprising methanol, light ends, water, and fusel oil; and
   b) passing said crude methanol stream in the presence of a diluent to an oxygenate conversion zone containing a SAPO catalyst selected from the group consisting of SAPO-34 and SAPO-17 to produce a light olefin product comprising ethylene, propylene, butylene, and water;
   c) separating said light olefin product to provide a by-product water stream, an ethylene product, a propylene product, and a butylene product; and
   d) returning at least a portion of said by-product water stream to said syngas production zone to provide a portion of said water stream and at least a portion of said diluent.

9. A process for the production of light olefins from a hydrocarbon gas feedstream, comprising methane and ethane, said process comprising:
   a) passing said feedstream in combination with a first water stream to a syngas production zone to produce a synthesis gas stream and passing said synthesis gas stream to an oxygenate formation zone to produce an oxygenate product stream comprising at least one of methanol or dimethyl ether;
   b) passing at least a portion of the oxygenate product stream in the presence of a diluent to an olefin production zone containing a SAPO catalyst selected from the group consisting of SAPO-34 and SAPO-17 to produce a light olefin stream consisting essentially of olefins having 2 to 4 carbon atoms per molecule and a second water stream;

c) admixing at least a portion of said second water stream with a make-up water stream to provide a water admixture and passing at least a portion of the water admixture to said syngas production zone to provide said water stream and at least a portion of said diluent;

d) passing said light olefin stream to a first fractionation zone to provide a methane stream, an ethylene product stream, and a $C_3^+$ stream;

e) passing said $C_3^+$ stream to a $C_3^+/C_4$ fractionation zone to provide a crude propylene stream, and a $C_4^+$ stream; and, f) passing a portion of said crude propylene stream and a portion of said second water stream to a first etherification zone to form a first ether product comprising diisopropyl ether and a first light ends stream.

10. The process of claim 9 further comprising:

a) passing said light olefin stream to a first fractionation zone to provide a methane stream, an ethylene product stream, and a $C_3^+$ stream; and b) passing said $C_3^+$ stream to a $C_3^+/C_4$ fractionation zone to provide a crude propylene stream, and a $C_4^+$ stream;

c) passing a portion of said crude propylene stream and a portion of said second water stream to a first etherification zone to form a first ether product comprising diisopropyl ether and a first light ends stream.

11. The process of claim 9 wherein said crude propylene stream comprises from about 90 to about 96 vol-% propylene.

12. The process of claim 9 further comprising:

a) passing the $C_4^+$ stream to a butylene fractionation zone to provide a n-butene stream essentially free of isobutene and a $C_5^+$ stream; and b) passing said n-butene stream to a super fractionation zone to provide an essentially pure butene-1 stream and a mixed butene stream and withdrawing the butene-1 stream.

13. The process of claim 12 wherein said $C_4^+$ stream comprises less than about 0.1 mol-% isobutene.

14. The process of claim 12 wherein said butene-1 stream comprises more than 90 mol % butene-1.

15. The process of claim 12 further comprising passing said ethylene product and at least a portion of said butene-1 stream to a polyethylene zone to produce a linear low density polyethylene product.

16. The process of claim 9 further comprising:

a) passing said $C_4^+$ stream to a $C_4$ fractionation zone to provide a mixed $C_4$ stream and a $C_5^+$ stream;

b) passing at least a portion of said mixed $C_4$ stream comprising normal butenes to a butene isomerization zone to isomerize said normal butenes and provide an isomerization stream comprising isobutenes; and c) admixing at least a portion of said isomerate stream with a portion of said oxygenate product stream to provide a second etherification feedstream and passing said second etherification feedstream to a second etherification zone to produce a second ether product comprising methyl tert. butyl ether.

17. The process of claim 16 further comprising admixing at least a portion of said mixed $C_4$ stream with said isomerate stream prior to admixing said mixed $C_4$ stream with said oxygenate product stream.

18. The process of claim 16 further comprising removing a butene-1 fraction from said mixed $C_4$ stream to said isomerization zone.

19. The process of claim 18 wherein said removing of the butene-1 fraction comprises fractionation when said mixed $C_4$ stream comprises less than about 0.1 mol-% isobutene.

20. The process of claim 18 wherein said removing of the butene-1 fraction comprises adsorbing said butene-1 fraction in an adsorption zone to provide a normal butene stream and an isobutene product stream, and passing said normal butene stream to a butene-1 fractionation zone to separate said butene-1 fraction from said normal butene stream.

21. The process of claim 9 further comprising passing said $C_4^+$ stream to a $C_4$ fractionation zone to provide a mixed $C_4$ stream and a $C_5^+$ stream and separating said $C_4$ stream into a butene-1 product stream and a mixed butene stream.

22. The process of claim 21 further comprising passing said mixed butene stream to a dimerization zone to produce a $C_8$ dimer.

23. The process of claim 22 further comprising hydrogenating said $C_8$ dimer to provide a $C_8$ alkylate stream.

24. The process of claim 23 further comprising blending said $C_8$ alkylate stream into a motor gasoline product.

25. The process of claim 22 further comprising reacting said $C_8$ dimer in the presence of carbon monoxide and hydrogen to produce a nonyl alcohol stream.

26. The process of claim 9 further comprising:

a) passing said $C_4^+$ stream to a second fractionation zone to provide a normal butene stream comprising less than 10 mol % isobutene and a $C_5^+$ olefin stream;

b) reacting said normal butene stream and a $C_4$ recycle stream in an isomerization zone to produce a butene isomerate stream and a second light ends stream;

c) passing said butene isomerate and at least a portion of said oxygenate product stream to a second etherification zone to produce a high octane ether comprising methyl tert. butyl ether and an unreacted $C_4$ stream; and d) returning at least a portion of said unreacted $C_4$ stream to the isomerization zone to provide said $C_4$ recycle stream.

27. The process of claim 26 further comprising blending at least a portion of said high octane ether and said first ether product into a motor gasoline stream.

28. The process of claim 9 wherein said hydrocarbon feedstream comprised a natural gas stream.

29. A process for the production of light olefins and high octane ether from a hydrocarbon gas feedstream comprising methane and ethane, said process comprising:

a) passing said feedstream and a first water stream to a syngas production zone to produce a synthesis gas stream comprising hydrogen and a carbon oxide, passing said synthesis gas stream to a methanol formation zone to produce a methanol product stream, and passing at least a portion of methanol product stream in the presence of a diluent to an oxygenate conversion zone containing SAPO catalyst at conditions effective to produce an effluent stream comprising olefins having 2 to 4 carbon atoms per molecule and water;

b) separating said effluent stream into an olefinic hydrocarbon stream and a second water stream and recycling at least a portion of said second water stream to said syngas production zone to provide a portion of said first water stream and at least a portion of said diluent; and c) fractionating said olefinic hydrocarbon stream by successive distillation to provide an ethylene product stream, a crude propylene stream, and a $C_4^+$ stream and etherifying said crude propylene stream with another portion of said second water stream to produce a diisopropyl ether stream.

30. The process of claim 29 wherein said crude propylene stream comprises more than about 90% mol-% propylene.

* * * * *